United States Patent
Schwitzer et al.

(10) Patent No.: US 9,682,211 B2
(45) Date of Patent: Jun. 20, 2017

(54) CATHETER SHAFT COMPRISING WELDED TUBES

(71) Applicant: Biotronik AG, Buelach (CH)

(72) Inventors: Alwin Schwitzer, Buelach (CH); Hans Lang, Buchs (CH)

(73) Assignee: Biotronik AG, Buelach (CH)

( * ) Notice: Subject to any disclaimer, the term of this patent is extended or adjusted under 35 U.S.C. 154(b) by 261 days.

(21) Appl. No.: 13/789,186

(22) Filed: Mar. 7, 2013

(65) Prior Publication Data

US 2013/0261604 A1    Oct. 3, 2013

Related U.S. Application Data

(60) Provisional application No. 61/617,059, filed on Mar. 29, 2012.

(51) Int. Cl.
*A61M 25/00* (2006.01)
*A61L 29/04* (2006.01)

(52) U.S. Cl.
CPC ....... *A61M 25/0009* (2013.01); *A61L 29/041* (2013.01); *A61M 25/0043* (2013.01)

(58) Field of Classification Search
CPC ... A61L 29/041; A61M 39/146; A61M 25/10; A61M 25/1034; A61M 25/1029
USPC .............. 156/294; 604/523, 524, 96.01, 103
See application file for complete search history.

(56) References Cited

U.S. PATENT DOCUMENTS

| | | | |
|---|---|---|---|
| 5,653,266 A * | 8/1997 | Reynolds | B29C 47/0023 138/137 |
| 6,659,977 B2 * | 12/2003 | Kastenhofer | A61M 25/00 604/264 |
| 2007/0158312 A1 * | 7/2007 | Wang | B23K 1/0004 219/59.1 |
| 2010/0063476 A1 * | 3/2010 | Quillin | 604/523 |
| 2010/0255378 A1 | 10/2010 | Bonnet et al. | |
| 2012/0203173 A1 * | 8/2012 | Davies et al. | 604/96.01 |

FOREIGN PATENT DOCUMENTS

| | | |
|---|---|---|
| AU | 2004202463 | 2/2005 |
| EP | 1484346 | 5/2012 |

OTHER PUBLICATIONS

European Search Report Dated Jan. 5, 2016.

* cited by examiner

*Primary Examiner* — Bhisma Mehta
*Assistant Examiner* — Hamza Darb
(74) *Attorney, Agent, or Firm* — Greer, Burns & Crain, Ltd.; Steven P. Fallon

(57) ABSTRACT

One embodiment of the invention relates to a catheter shaft comprising (i) a first tube made of an extrudable copolymer that has reactive groups, and (ii) a second tube made of a polymeric material, which can be welded to the first tube, wherein the polymeric material of the second tube can be welded to the first tube at a temperature $\leq 200°$ C.

23 Claims, 6 Drawing Sheets

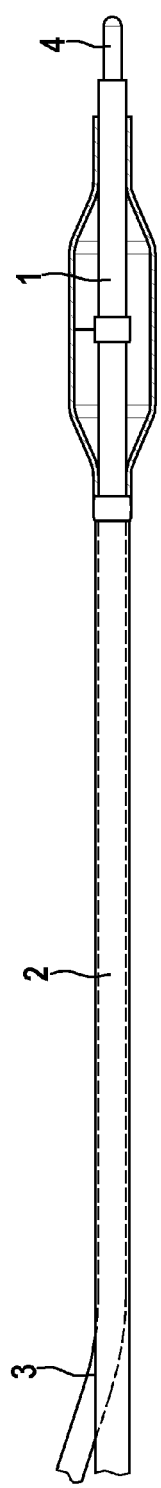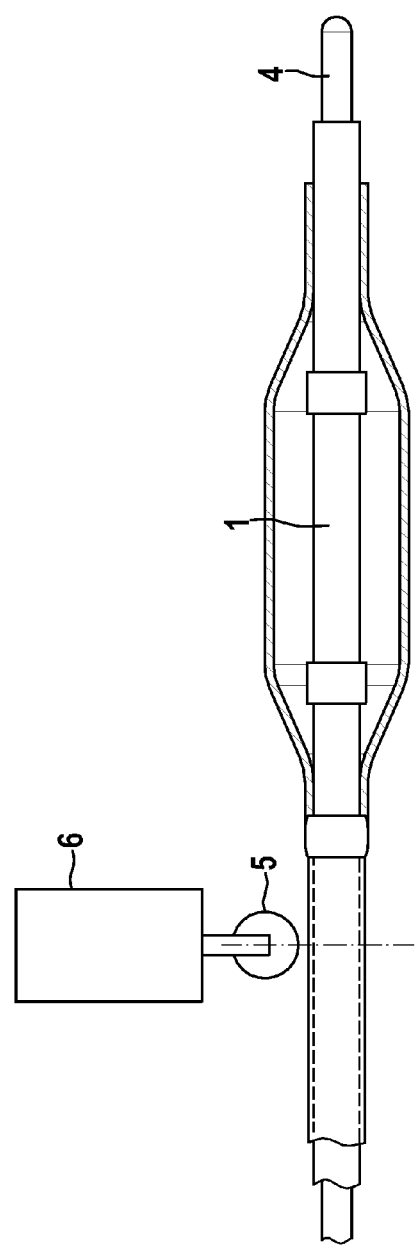

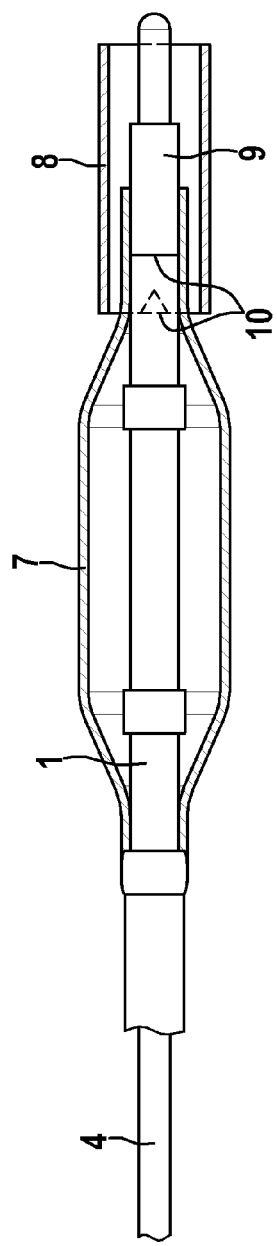
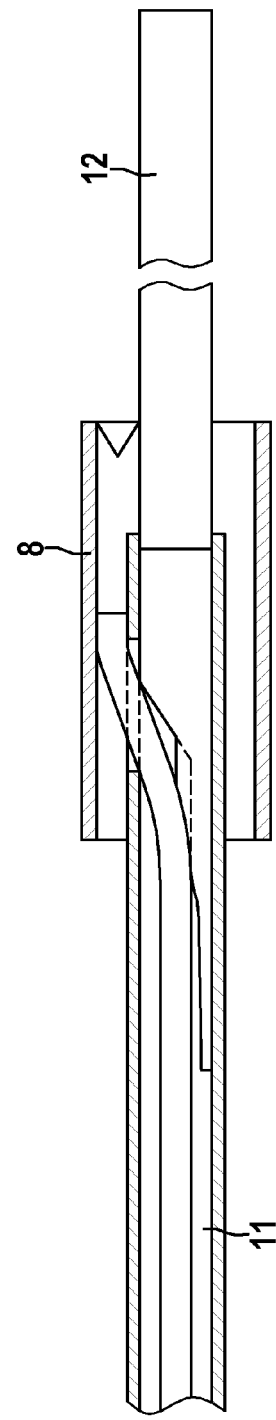
FIG. 5
FIG. 6

CATHETER SHAFT COMPRISING WELDED TUBES

CROSS REFERENCE

The present application claims priority on U.S. Provisional Application No. 61/617,059 filed on Mar. 29, 2012; which application is incorporated herein by reference.

TECHNICAL FIELD

A field of the invention is catheters. Another field of the invention relates to a catheter shaft comprising a first (inner and/or outer) tube made of an extrudable, fluorinated copolymer and a second tube made of a polymeric, preferably thermoplastic, material, which is welded to the first tube.

Another field of the invention further relates to a medical device comprising such a catheter shaft, and the use of a first tube made of an extrudable, fluorinated copolymer to be welded to a second, polymeric tube. Another field of the invention also relates to a method for manufacturing a catheter shaft or a medical device comprising the related tubes and a certain, particularly suitable tube.

BACKGROUND

On the market today, multi-layer tubes are used for the inner shaft of a catheter. They include, for example, multi-layer polytetrafluoroethylene (PTFE) tubes, co-extruded HDPE (high density polyethylene) tubes and the like, which comprise a polyamide-based outer layer to permit these inner shafts to be welded to other tubes that have a second tube layer made of a polymeric, thermoplastic material.

Fluorinated polymers (e.g., PTFE) generally have the lowest coefficients of friction relative to other materials, are resistant to ageing and are highly resistant to chemicals. Disadvantages of PTFE are the complex manufacturing process of tubes (not by conventional extrusion since PTFE cannot be processed thermoplastically because PTFE is not fusible) and the low abrasion resistance. Another disadvantage of PTFE-based inner tubes is the high price and the dependence on certain manufacturers. A further disadvantage of PTFE as a material for medical devices is that PTFE cannot be sterilized using radiation sterilization methods.

Other thermally deformable (extrudable), fluorinated polymers that also have low coefficients of friction (for example, ETFE (polytetrafluorothylene+ethylene, E-CTFE (polychlorotrifluoroethylene+ethylene), PFA (polytetrafluoroethylene+perfluoropropylether), FEP (polytetrafluoroethylene+perfluoropropylene), PCTFE (polychlorotrifluoroethylene), PVF (polyvinyl fluoride) and PVDF (polyvinylidene fluoride)) cannot be welded to the established catheter polymers (such as polyamide 12 or PEBA, for example), which are used for outer shafts, tips and balloons, for instance, and are very difficult to bond due to the low surface tension and resulting reduced wettability.

For this reason, only highly complex, multi-layer tube structures have become established for use as inner shafts for RX catheters (with reduced friction with respect to guide wires), for example. Tubes are known, inter alia, which have PTFE as the inner layer and a polyamide-based outer layer or multi-layer structures having an HDPE inner layer and, likewise, a polyamide-based outer layer.

The disadvantage of co-extruded inner shaft designs based on HDPE, for example, is also the expensive manufacturing process by co-extrusion of at least two, typically three layers, in which one extruder is used for each layer.

Document US 2010/0063476 A1 describes the use of modified PVDF as the inner layer of co-extruded tubes. Co-extrusion requires the use of highly complex equipment and requires working with at least two, typically three separate extruders, which must be matched to one another, to ensure that the two or three co-extruded layers have the desired layer thickness distributions in the final tube dimensions. The temperatures of the separate extruders must be selected such that the different tube layers are connected to one another during extrusion, which, in the case of a 3-layer extrusion, typically takes place by way of a physical connection between the HDPE inner layer to the middle layer and by way of a chemical connection of the middle layer to the polyamide-based outer layer. The pressure and temperature requirements are therefore high. Co-extrusion results in covalent bonding of the two tube layers, which is absolutely desired.

SUMMARY

One of the problems addressed by the invention was that of providing catheter shafts that could be manufactured more easily, at a lower cost, that preferably have the lowest possible coefficient of friction, and preferably have high chemical resistance and/or high ageing resistance. In addition, through methods of the invention it is possible to weld these shafts to typical polymer-based catheter components, in particular components based on polyamide. A further preferred property is for the components to be effectively sterilizable using radiation.

This and other problems are solved by a catheter shaft comprising (i) a first (inner and/or outer) tube made of an extrudable copolymer that has reactive groups, and (ii) a second tube made of a polymeric material, which can be welded to the first tube, wherein the polymeric material of the second tube can be welded to the first tube at a temperature ≤200° C.

BRIEF DESCRIPTION OF THE FIGURES

FIG. 3 is a schematic drawing of the design of a catheter comprising an inner shaft according to the invention FIG. 4 is a schematic drawing of the welding of the outer shaft and inner shaft FIG. 5 is a schematic drawing of a distal balloon welding at a catheter shaft according to the invention FIG. 6 is a schematic drawing of the proximal welding of a distal catheter according to the invention to a hypotube

DETAILED DESCRIPTION

Figure 1:
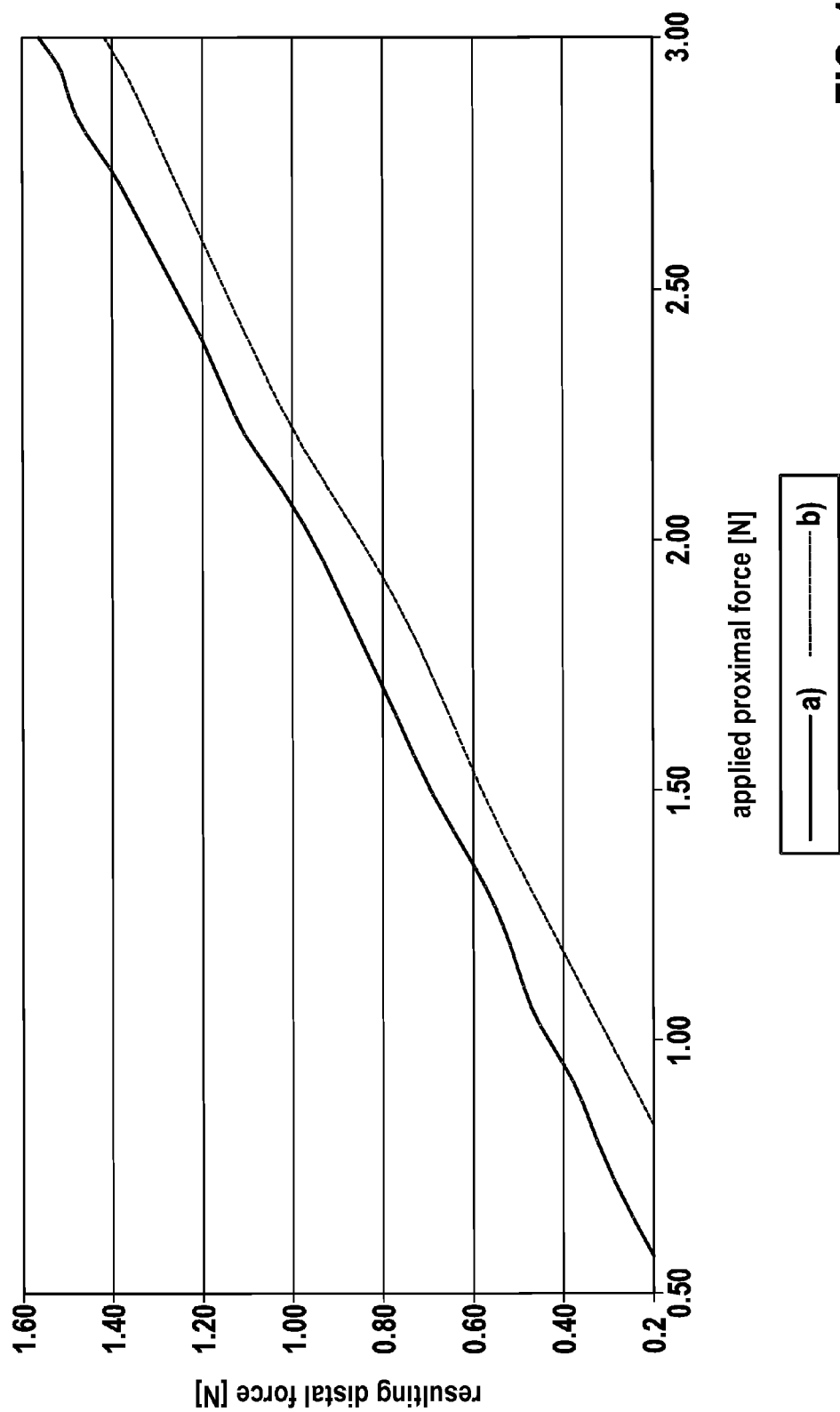
FIG. 1 shows the pushability (force transmission) on coronary balloon dilation catheters comprising
  a) a balloon dilation catheter having an inner shaft according to the invention
  b) balloon dilation catheter having a co-extruded inner shaft with HDPE as the inner layer, according to the prior art
    The figure therefore shows a comparison of the mechanical forces that play a role in the forward motion of a catheter shaft according to the invention, compared to a shaft according to the prior art.

Before discussing various example embodiments and features of the invention, some discussion of definitions of terms used in such description will be useful. It will be appreciated that unless otherwise stated, terms are intended to have their ordinary meaning in the broadest sense.

Reactive groups are molecular groups that have a higher reactivity to nucleophiles than methyl or methylene groups. Within the scope of the invention, reactive groups preferably have at least the reactivity of a carbonyl group, particularly preferably from a carbonic acid derivative group, most particularly preferably from a carbonic acid anhydride group, with respect to nucleophilic agents, preferably with respect to a hydroxy and/or amine group. A copolymer within the scope of the present invention can already be present if only reactive groups are incorporated into a classical polymer parent structure. It is also possible, in principle, for side chains carrying the more reactive groups to be bound to the polymer parent structure, preferably being grafted thereto.

Within the scope of the present invention, welding means that two layers (in this case, the outer layer of one tube and the inner layer of another tube in particular), which are substantially in the solid state, are covalently bound by the (relatively brief) effect of heat. Within the scope of the invention, it is not ruled out that (brief) softening caused by fusion takes place in the region of the interfaces of the two layers.

Within the scope of the invention, welded means that at least one spot weld is present, that is, the first and second tubes within the scope of the present invention do not need to be welded to one another in a flat manner, but rather that spot welded connections are sufficient within the scope of the invention (although in some embodiments "welded" may refer to flat welding of two pieces to one another). Welded connections are preferable, however, which interconnect at least the entire circumference in the region of a tube section (that is, of a part of the longitudinal extension of the tube). This means that, strictly speaking, the lumen of the outer tube welded to the inner tube no longer needs to be continuous.

Within the scope of the present invention, extrudable means that the (dried) material (preferably a thermoplastically shapable polymer or copolymer) can be fused in a single-screw extruder having a diameter of 12 to 30 mm and a length-to-diameter ratio (L/D) of 24 to 28 at temperatures that are 50° C. to 100° C. higher than the melting point of the thermoplastic polymers, the polymer melts are conveyed to a shaping part (extrusion head) comprising a nozzle, which shapes the outer tube layer, and a mandrel, which shapes the inner tube layer, and can be brought into a permanent shape by "quenching" the shaped polymer melts in a water bath.

It has been shown that suitable modified fluorinated polymers (copolymers) are capable of bonding with sufficient strength to a plurality of preferably thermoplastic, polymeric materials that preferably have nucleophilic groups. In the prior art, such compounds were regularly created by co-extrusion, however. Through the present invention it has been discovered, surprisingly, that it is possible to weld a hardened tube made of a fluorinated copolymer comprising reactive groups to a plurality of suitable second separate tubes at temperatures ≤200° C. Before the invention, it was assumed that the appropriate materials could only be bound to one another in an adequate manner by way of co-extrusion which added significant cost, time and effort as compared to embodiments of the invention.

Preferably at least the first tube, but further preferably both tubes, are present as separate tubes when welding takes place. Welding preferably takes place over the greatest possible surface area, which means that the two tubes have different diameters, thereby enabling one tube to be slid into the other tube (although in some embodiments local spot weld connections may be used). The inner diameters and wall thicknesses of the tubes must be suitably matched to one another, with at least some embodiments including an outer tube inner wall surface contacting the inner tube outside wall surface and other embodiments allowing for some suitably small gap between walls to exist. A flat weld along the outer circumferential surface (of the inner tube) or the inner circumferential surface of the outer tube is preferable.

The invention relates to the configuration in which the first tube is attached to the outer tube, and to the configuration in which the first tube is the inner tube. Further layers and/or tubes are present in other embodiments, although in many applications the catheter shaft will comprise only the first tube and the second tube.

On the basis of the present application it is possible for a person skilled in the art to match materials and welding surface sizes such that the weld points are highly stable. Within the scope of the invention, however, these welds are preferably designed such that they resist, without changing, a balloon pressure of 20 bar, preferably 24 bar, for ≥1 min, preferably ≥2 min, particularly preferably ≥10 min. A person skilled in the art will also take the entire geometry of the weld surfaces into account for this purpose.

According to one embodiment of the invention, a catheter shaft is preferred, wherein the fluorinated copolymer is a thermoplastic copolymer on the basis of a polymer selected from the group comprising ETFE, C-ETFE, PFA, FEP, PCTFE, PVF and PVDF.

A changed PVDF that has been modified preferably by the grafting of maleic acid anhydride is particularly preferred in this context.

Documents AU 2004/202463 B2 and EP 1 484 346 and US 2010/0255378 A1 all disclose copolymers of fluoropolymers (modified fluoropolymers), at least some of which are examples of materials that may be useful in practice of some invention embodiments. These documents are incorporated herein by reference to the extent necessary and possible as examples of materials that may be useful to practice some invention embodiments. Those knowledgeable in the art will appreciate many such materials as generally described herein are available, and detailed description thereof is not necessary for sake of brevity.

The aforementioned materials are suitable in particular due to their chemical resistance and their low coefficient of friction. The aforementioned copolymers can be extruded as the first tube, and can be used as either the inner tube or the outer tube, depending on the intended use of the catheter shaft or the medical device comprising said catheter shaft. Extrusion may be single extrusion of a single layer tube.

In general, thermally deformable, fluorinated polymers are preferred, in addition to the explicitly named fluorinated polymers, for the first tube (in a related modification).

Preferred reactive groups in the fluorinated copolymer for bonding to the second tube are in the groups (chemical functions) selected from the group comprising carbonic acid, carbonic acid chloride, amide, carbonic acid anhydride, ester, lactone, lactam, nitrile, and thioester.

By way of these reactive groups, nucleophilic attacks on the polymeric material of the second tube are well ensured, and therefore a plurality of material combinations is possible.

Within the scope of the present invention it is preferable for the second tube to be selected from the group of polyamide, PEBA (polyether block amide), polyester, thermoplastic polyurethane elastomers (TPU).

In general, thermoplastic polymers are preferred for the second tube.

As indicated above, it has surprisingly been discovered that the modification of the fluorinated polymers makes it possible to establish a reliable connection to the polymers of the second tube. Within this context it was surprising, however, as likewise indicated above, that welding can be carried out even under relatively mild conditions, and that co-extrusion is not absolutely necessary (although it may be used in some invention embodiments).

Further material combinations are usable due to the invention, thereby providing a person skilled in the art with more possibilities with respect to the prior art for adapting the catheter shaft or medical devices containing them to the particular requirements. It is possible, for example, to design the inner shafts for RX catheters (with reduced friction with respect to guide wires) without the need for complex multi-layer tube structures comprising intermediate primer layers. There is also a good alternative to PTFE as the inner layer, and there are alternatives to the typical HDPE inner layers on the market. Valuable benefits, including cost savings and improved performance, are thereby achieved over the prior art.

The mechanical properties of the complete system can also be improved by way of the combination according to the invention.

Turning now to the drawings by way of further illustration, compared to a balloon dilation catheter having a co-extruded HDPE inner shaft, a (balloon dilation) catheter according to the invention has a higher transmission of the force applied at the proximal end onto the distal end of the catheter (FIG. 1).

Figure 2A:
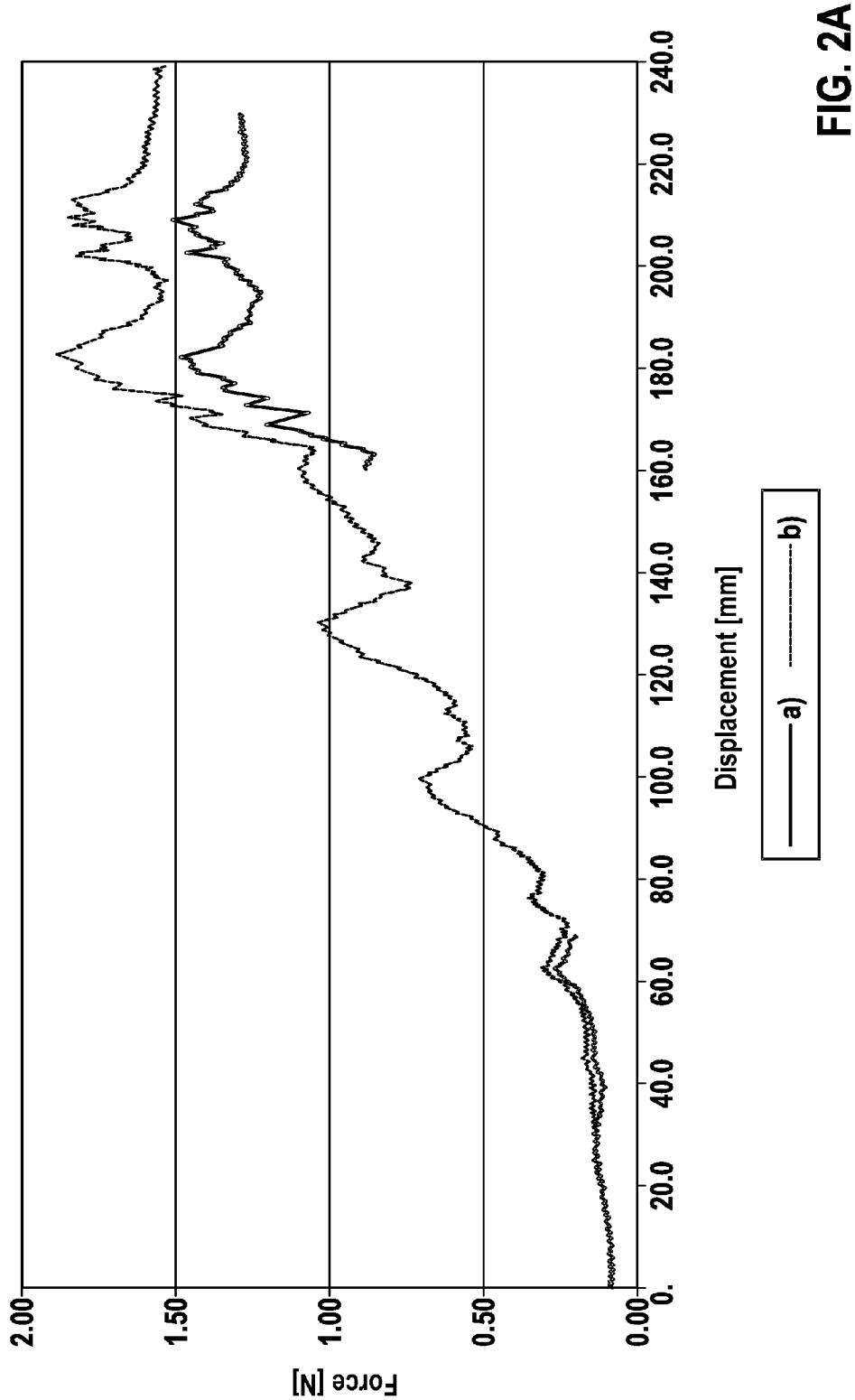
FIGS. 2a and 2b show the trackability (frictional forces) on coronary balloon dilation catheters in an aorta model with a Teflon® tube as the friction partner. Guide wire: Galeo M "014; guide catheter: Cordis Vista 5F JL 4LBT
  a) a balloon dilation catheter having an inner shaft according to the invention
  b) a balloon dilation catheter having a co-extruded inner shaft (US 2010/0063476 A1
  FIGS. 2a and 2b therefore present corresponding data on friction.
Figure 2B:
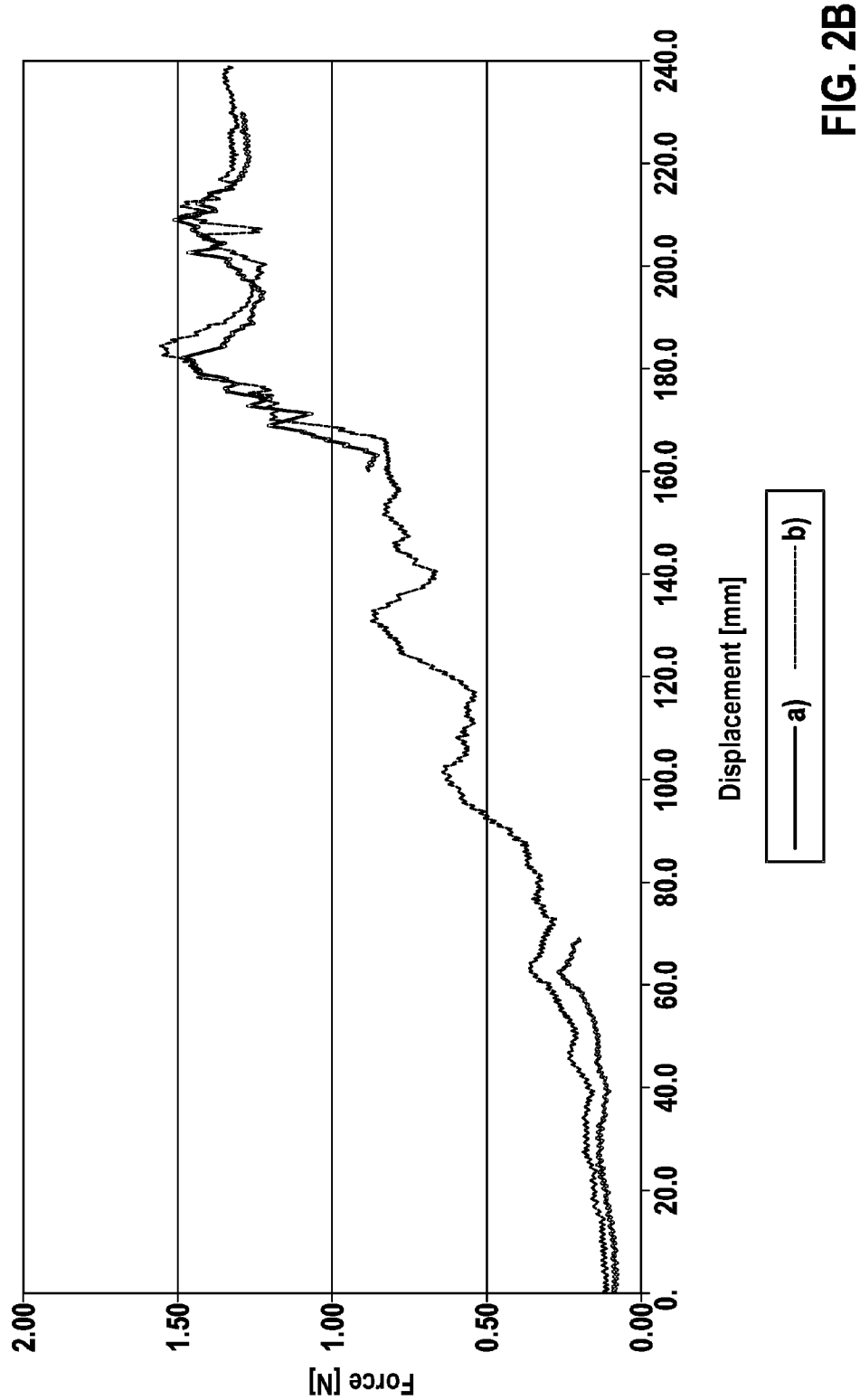

FIG. 2a shows a comparison of the frictional forces of a balloon dilation catheter according to the invention with those of a balloon dilation catheter of the prior art according to US 2010/0063476 A1. The two balloon dilation catheters are identical except that the inner shafts are different. In this test, the catheters are introduced in vitro in a model that corresponds to a simulation of a coronary artery, and the required proximal force is determined. The balloon dilation catheter according to the invention requires much less force than the catheter according to US 2010/0063476 A1, which indicates lower friction in the case of the inner shaft according to the invention compared to the catheter according to US 2010/0063476 A1. The balloon dilation catheter according to the invention also exhibits slightly improved frictional forces compared to a catheter comprising a co-extruded HDPE inner shaft according to the prior art (FIG. 2b). This illustrates a few of the many valuable benefits and advantages embodiments of the invention achieve over the prior art.

According to the above-cited tests, a first tube is particularly preferred, according to the invention, for a single-layer catheter shaft made of a PVDF grafted with maleic acid anhydride, which is fused in a conventional single-screw extruder (Ø 12-30 mm/L/D 24-28) and is shaped into a tube by way of a shaping part. The shaped melt is quenched in a water bath. The second tube, which can be welded to the first tube, comprises a polyamide layer, preferably an (initially) separate tube.

A fluorinated copolymer that may be used includes polyvinyldene fluoride (PVDF). In some applications, a functionalized PVDF is used that has a reactive group. A useful example is the material with the trade name "Kynar® ADX" from the company Arkema Inc., (King of Prussia, Pa.). Tubes can be produced from this material by extrusion at low cost.

Kynar ADX was developed by Arkema for the co-extrusion of PVDF with polyamide 12, for automobile fuel lines, for example. Kynar ADX is a functionalized polyvinylidene fluoride, which can enter into a chemical bond with thermoplastic polymers, such as polyamide, PEBA, polyester, TPU, etc. The reactive functional groups of maleic acid anhydride are introduced into the original PVDF by compounding and slight irradiation cross-linking. In US 2010/0063476 A1, this material is used for the co-extrusion of a two-layer tube in accordance with the manufacturer's field of application.

The chemical modification of a PVDF such as Kynar ADX is intended to produce a chemical bond when two polymer melts meet in the co-extrusion process, for example, in is which the maleic acid anhydride of the Kynar ADX is attacked by way of nucleophilic groups of the second layer, wherein at least one amide bond, preferably an imide bond, is produced.

Surprisingly, tubes made of a functionalized PVDF such as Kynar ADX can also enter into a chemical bond with other polyamide-based components (welding) after thermal treatment. That is, the chemical modification also functions after extrusion and the immersion of the shaped Kynar ADX melts associated therewith in water. This is previously unknown for this material since the maleic acid anhydride groups at the tube surface, which have contact with water, are saponified to form less reactive dicarbonic acid groups. By slightly fusing the surfaces of the two elements to be joined (the first and second tubes in this case), a covalent chemical bond is created between the two elements to be joined. This is sufficient to weld the various components to one another.

PVDF also has better radiation sterilizability than PTFE (maximum radiation dosage PVDF 1500 kGy, Teflon <20 kGy).

These first tubes according to the invention, which are made of PVDF, can be used as the inner tube for RX catheters, for example (although in some other example embodiments they can be the outer tube). They can be chemically welded proximally with a polyamide-based outer shaft and distally to a polyamide-based balloon and/or tips, in particular by way of a laser or thermal energy.

Alternatively, it is also possible to use the corresponding first tube as the outer tube for RX catheters without coating, or as the outer tube for self-expandable stent delivery devices. In this case, the low friction of the material is utilized toward the outside in particular. The advantages of the catheter shafts according to the invention to be emphasized in particular are, therefore:

Single extrusion of the first tube can be carried out without co-extrusion. This results in considerable cost savings, in particular with regard to the extrusion devices and conditions.

The friction of the first tubes (in particular in the preferred shapes) is greatly improved (reduced) in the form of an outer tube and as an inner tube within a catheter tube.

The mechanical properties related to introducibility are improved.

Reliable sterilization by radiation is possible.

The first tube made of modified PVDF can be welded to polyamide-based second tubes by way of chemical binding.

Moreover, it is possible to easily weld further components to the catheter shaft.

Part of the invention is therefore a medical device comprising a catheter shaft, as described above.

Particularly preferably, such a medical device is selected from the group comprising a catheter stent insertion device or a balloon dilation catheter, in particular in an RX (rapid exchange) or "over the wire" design.

Part of the invention is also a (first) tube made of a PVDF grafted to maleic acid anhydride as the reactive group, which was fused, in particular, in a conventional single-screw extruder (Ø 12-30 mm/L/D 24-28) and shaped into a tube by way of a shaping part, and which can be welded in particular to a second polyamide-based tube, a separate tube, as a component of a catheter shaft according to the invention or a medical device according to the invention.

In the case of the material that is used particularly preferably according to the invention, although a scientific basis for the discovery is not presently known with certainty, it is believed that the reactive group (maleic acid anhydride) is hydrated in water after is extrusion, and therefore a chemical reaction with amino groups, for example, is possible even when welding is performed at ≤200° C., and in others less than 190° C., and in some embodiments at pressures less than 200 bar, others less than 180 bar, in contradiction to the accepted practice of the prior art (as indicated, for instance, by a PVDF manufacturer's claim). Prior to the present invention it was believed that temperatures >220° C. and pressures in the range of 200 bar were required to ensure reliable bonding of the material to a corresponding second tube. Under these conditions, the maleic acid anhydride reacts with amino groups of a polyamide and forms chemical imide compounds.

Using methods of the invention, however, this is not necessary. When welding is carried out in an invention embodiment, a carbonic acid function reacts with the amine to form an amide group. Therefore, only slight fusing is required during welding (T≤200° C.), wherein a shrink tube is preferably used in principle for welding, in order to press the tubes onto one another.

Compared to the prior art, this has the following valuable benefits and advantages (among others):

In the 3-layer co-extrusion of HDPE/primer/polyamide inner tubes, the three different materials are fused in three different extruders at different temperatures. The three polymer melts are guided to a shaping part (co-extrusion head), where the three polymer melts meet. A physical bond is produced between the HDPE and the primer layer, and a chemical bond is produced between the polyamide layer and the primer layer. In this design, the HDPE inner layer serves to minimize friction with respect to the guide wire. The primer layer joins the HDPE inner layer with the polyamide outer layer. The polyamide outer layer serves for bonding with other polyamide-based tubes, tips or balloon (=component to be welded thereto). The same mode of operation also takes place in the co-extrusion of the inner shaft in the laid-open application US 2012/0063476 A1. In this case, the inner layer is made of the fluorinated modified polymer PVDF, which is bonded to the polyamide-based outer layer by way of the chemical modification in the co-extrusion. The PVDF inner layer serves to reduce the friction with respect to the guide wire, and the polyamide-based outer layer serves to ensure weldability to further polyamide-based tubes, balloons or tips. A physical welding of the two elements takes place, in which physical intermixing takes place by way of the fusion of the two surfaces to be connected.

In the extrusion of the modified PVDF according to some embodiments of the invention, only one single-layer tube is extruded, that is, the inner surface and outer surface of the tube is made of the modified PVDF. The welding with further catheter components (such as further tubes, balloons or tips) takes place by way of the chemical reaction of the maleic acid anhydride groups contained therein or the maleic acid groups that form with nucleophilic groups contained in the polymers of the separate welding partner. The two surfaces to be joined are therefore chemically interconnected by way of amide or imide bonds, and exhibit no intermixing.

In the conventional inner shaft design having physical intermixing of the two surface materials, the welding partners therefore differ fundamentally from the chemical welding of the two surface materials according to the invention (without intermixing of the two materials).

As described above, the catheter shafts according to the invention—and, therefore, medical devices according to the invention—have better trackability with respect to a catheter having a conventional three-layer HDPE inner shaft. Moreover, the transmission of force onto the distal end of the catheter is markedly increased compared to the conventional three-layer HDPE inner shaft. As a result, the dimensions (outer diameter) of the inner shaft can be reduced without making great sacrifices with respect to force transmission. In addition, the profile of crimped stents of stent delivery RX catheters is reduced.

Furthermore, it has been discovered that it is easily possible to reliably weld further components to the catheter shaft design according to the invention, such as distal balloons. In the catheter obtained in the example (see below), the distal balloon neck withstands pressures of at least 24 bar after being welded to the first tube (which was designed as an inner shaft) to be used according to the invention. The balloon burst at this pressure. This corresponds to an approximate minimal tension at the weld of 230-240 N/mm$^2$.

The increased force transmission (pushability) compared to conventional RX catheters having three-layer inner tubes (HDPE-Tie-PA or PEBA) improves the usability of the catheter shafts according to the invention or the medical devices that comprise said shafts.

If the first tube to be used according to the invention is used as a distal outer shaft, lower frictional properties exist without the need to apply an additional, complex and expensive coating.

Since sterilization by radiation is possible, the catheter shafts according to the invention can also be used for drug-coated cathers (drug-eluting stents or drug-eluting balloons), for example, in the case of which the drug that is applied cannot be sterilized by ethylene oxide.

According to the statements provided above, part of the invention is the use of a first tube, as defined above, for welding to a second tube, as likewise described above, to produce a catheter shaft according to the invention or a medical device according to the invention.

This usage achieves the above-described advantages as well as others.

Another part of the invention is a method for the manufacture of a catheter shaft according to the invention or a medical device according to the invention, comprising the steps:
a) provide a first tube as defined above,
b) provide a second tube as defined above and
c) weld the first tube to the second tube.

By way of this method, the catheter shafts according to the invention and the medical devices according to the invention can be produced in a low-cost and reliable manner.

A method according to the invention is preferred, wherein welding takes place at a temperature ≤200° C.

These welding conditions are relatively mild, and it is therefore easily possible to produce the products according to the invention.

Moreover, a method according to the invention is preferable, wherein the first tube is provided by conventional tube extrusion with cooling of the shaped layer in water. PVDF grafted with maleic acid anhydride is preferably used, which, in turn, is preferably fused in a conventional single-screw extruder (Ø 12-30 mm/L/D 24-28) and shaped by way of a shaping part into a tube, which is quenched in a water bath.

As described above, when several reactive groups are present, in particular maleic acid anhydride, this mode of operation results in increased reactivity and, therefore, improved weldability even if the non-hydrated anhydrides are more reactive to nucleophiles than the dicarbonic acid groups that are produced.

Even further preferred is a method according to the invention, wherein the welding takes place by the effect of heat for 3-20 seconds, more preferably for 5-15 seconds.

This welding period is sufficient, and therefore a relatively rapid method for producing the objects according to the invention is made possible.

According to the invention, a method according to the invention is furthermore preferred in which welding takes place by way of heating jaws, laser, white light or vibration.

These are common means for welding which are easy to use and can be used extremely well for a number of variant applications.

EXAMPLES

Some example embodiments and features of the invention are explained in greater in the following with reference to examples and the related figures.

The figures show:
FIG. 1 the pushability (force transmission) at coronary balloon dilation catheters
FIGS. 2a and 2b the trackability (frictional forces) at coronary balloon dilation catheters in an aorta model with a Teflon® tube as the friction partner
FIG. 3 a schematic drawing of the design of a catheter comprising an inner shaft according to the invention
FIG. 4 a schematic drawing of the welding of the outer shaft and inner shaft
FIG. 5 a schematic drawing of a distal balloon welding at a catheter shaft according to the invention
FIG. 6 a schematic drawing of the proximal welding of a distal catheter according to the invention to a hypotube
FIG. 7 a schematic drawing of a proximal balloon welding The first tube was typically extruded from a chemically modified PVDF (e.g., Kynar ADX 1740-15 (PA) from Arkema) on a conventional single-screw extruder (e.g., Ø 12-30 mm with a L/D ratio of ~24).

1. Extrusion of a Single-Layer Tube to be Used According to the Invention

The granulate Kynar ADX 1740-15 (PA) was dried in a compressed air drier (dew point~–30° C.) for 4-6 h at 70-100° C.

The dried granulate was metered into the extruder by way of the intake zone of a single-screw extruder (Ø 12-30 mm, L=24-28 D) and fused in the extruder at the temperatures is proposed by Arkema. The melts were conveyed out of the extruder by way of an extrusion head comprising a nozzle and a mandrel, and the tube shaped in this manner was calibrated to the desired final tube dimension, wherein a draw-rate balance of approximately ~1.0 and a deep-draw ratio of 8-10 were used.

The resulting tube was characterized by tension testing:
Yield stress: 46 N/mm$^2$
Yield strain: 6%
Stress at failure: 100 N/mm$^2$
Percent elongation at failure: 254%
Modulus of elasticity: 1120 N/mm$^2$ 2. Welding of Inner Shaft Tube/Outer Shaft Tube FIG. 3 shows a schematic depiction of a catheter shaft according to the invention (catheter with an inner shaft according to the invention). The reference characters mean:
1 first tube (inner tube)
2 second tube (outer tube)
3 guide wire outlet point
4 auxiliary wire After the first tube 1 produced according to 1.) was inserted into the second tube 2 by way of the guide wire outlet point 3 thereof, an auxiliary wire 4 was inserted into the first tube 1.

FIG. 4 presents a schematic depiction of the procedure for welding the first tube and the second tube (outer tube and inner tube) together. The reference characters mean:
1 first tube
4 auxiliary wire
5 Si tube to prevent the outer tube 2 from fusing with the welding jaw 6.
6 welding jaw The first tube 1 (inner tube) was welded to the second tube 2 (outer tube) using the welding jaw 6 at welding jaw temperatures of 185-205° C. for 5-15 seconds.

3. Distal Balloon Welding

FIG. 5 presents a schematic depiction of the welding of a distal balloon to the catheter shaft according to the invention. The reference characters mean:
1 first tube
4 auxiliary wire
7 balloon
8 shrink tube
9 tip
10 flush lay edge A suitable auxiliary wire 4 was inserted into the first tube 1. A so-called tip 9 made of polyamide was positioned on said auxiliary wire on the distal end of the first tube 1 (inner shaft). The distal balloon neck was positioned by way of the distal end of the first tube 1 and the proximal end of the tip 9. A shrink tube 8 was positioned by way of the distal balloon neck. The distal balloon neck was welded using a laser having a power of 20-25 watts within 4-7 seconds onto the first tube 1 and the tip 9, wherein the region to be welded rotated in the axial direction at 1,500-2,500 rpms.

4. Welding the Guide Wire Outlet Points

The distal part produced according to 3.) was now connected to the proximal part of a hypo tube. This is depicted schematically in FIG. 6. The reference characters mean:

8 shrink tube
11 front part of the catheter
12 hypotube

To this end, the second tube 2 was slid with the first tube 1 onto the hypotube encased in polyamide by way of a shrink tube. The second tube 2 was then welded using welding jaws for 8-20 seconds at 215-235° C. At the same time, the first tube 1 was also welded to the second tube 2.

5. Proximal Balloon Welding

Figure 7:
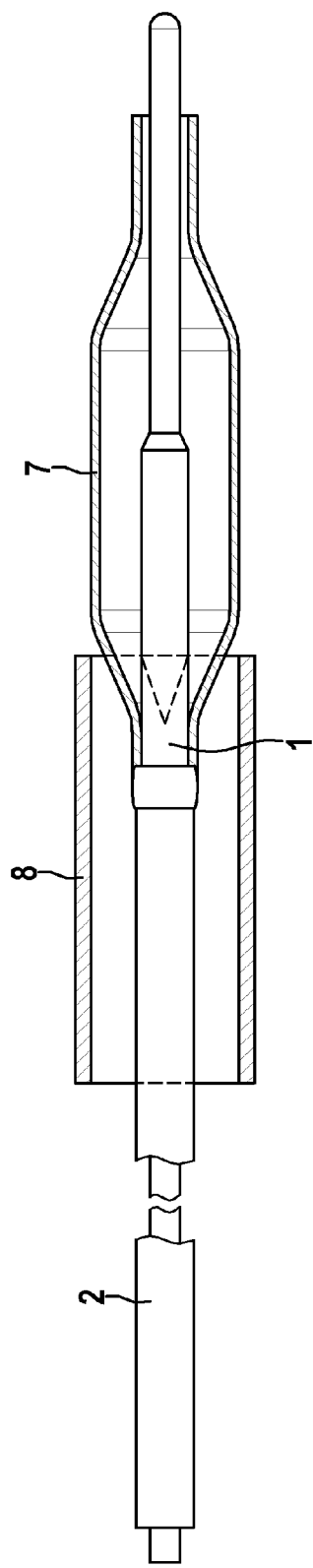
FIG. 7 is a schematic drawing of a proximal balloon welding

FIG. 7 shows the proximal balloon welding in a schematic depiction. The reference characters mean:

1 first tube
2 second tube
7 balloon
8 shrink tube

An appropriate wire was inserted into the second tube 2 and the proximal balloon neck was positioned on the distal end of the second tube 2 (outer shaft). A shrink tube 25 was positioned over the point to be welded. A balloon neck was welded onto the second tube 2 using a laser for 1 to 4 seconds with an energy of 15 to 25 watts. Next, the shrink tube was removed.

All of the welds created above were checked in a pressure test. None of the welds described failed, having been exposed to pressures of at least 24 bar.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A catheter shaft comprising
(i) a first tube made of an extrudable fluorinated copolymer that has reactive groups, and (ii) a second tube made of a polymeric material, which is welded to the first tube, wherein a lumen of the second tube is welded to the first tube with a flat weld or a plurality of local spot welds along a circumference of the catheter shaft, and the diameters and wall thicknesses of the first tube and the second tube are matched to one another such that the outer wall surface of the first tube contacts the inner wall surface of the second tube or leaves a small weld gap between the first tube and the second tube.

2. The catheter shaft according to claim 1, wherein the fluorinated copolymer is a copolymer of a polymer selected from the group comprising ETFE (polytetrafluorothylene+ethylene), C-ETFE (polychlorotrifluoroethylene+ethylene), PFA (polytetrafluoroethylene+perfluoropropylether), FEP (polytetrafluoroethylene+perfluoropropylene), PCTFE (polychlorotrifluoroethylene), PVF (polyvinyl fluoride) and PVDF (polyvinylidene fluoride).

3. The catheter shaft according to claim 1, wherein the reactive groups are selected from the group comprising carbonic acid, carbonic acid chloride, amide, carbonic acid anhydride, ester, lactone, lactam, nitrile and thioester.

4. The catheter shaft according to claim 1, wherein the polymeric material of the second tube is selected from the group comprising polyamide, PEBA (polyether block amide), polyester or TPU (thermoplastic polyurethane elastomers).

5. The catheter shaft according to claim 1, wherein the first tube is made of PVDF (polyvinylidene fluoride) grafted with maleic acid anhydride as one of the reactive groups, and the second tube is made of polyamide 12 or PEBA (polyether block amide).

6. The catheter shaft according to claim 1, wherein the tubes remain welded to one another, unchanged, at a pressure of 20 bar for ≥1 min.

7. The catheter shaft according to claim 1, wherein the catheter shaft is included in a medical device.

8. The medical device according to claim 7, selected from the group comprising a catheter stent insertion device or a balloon dilation catheter, in particular in an RX (rapid exchange) or over the wire design.

9. The catheter shaft as defined by claim 1 wherein the first tube is made of PVDF (polyvinylidene fluoride) grafted with maleic acid anhydride as one of the reactive groups.

10. The catheter shaft according to claim 1, wherein the polymeric material of the first and second tubes are configured to achieve welded attachment with welding performed at a temperature ≤200° C.

11. The catheter shaft according to claim 1, wherein the first and second tube are welded with a plurality of spot weld connections.

12. The catheter shaft according to claim 1, wherein the first and second tube are welded to interconnect at least an entire circumference of the first and second tube in the region of at least one tube section.

13. The catheter shaft according to claim 1, wherein at least a portion of an outer surface of the first tube is welded to at least portion of an inner surface of the second tube.

14. The catheter shaft according to claim 1, wherein the first tube is arranged as an inner tube made of fluorinated modified PVDF (polyvinylidene fluoride) and the second tube is arranged as an outer tube made of a thermoplastic polymer material.

15. A catheter shaft comprising
(i) a first tube made of an extrudable fluorinated copolymer that has reactive groups, and (ii) a second tube made of a polymeric material, which is welded to the first tube, wherein a lumen of the second tube is welded to the first tube with a flat weld or at least one spot weld, and the diameters and wall thicknesses of the first tube and the second tube are matched to one another such that the outer wall surface of the first tube contacts the inner wall surface of the second tube or leaves a small weld gap between the first tube and the second tube.

16. The catheter shaft according to claim 15, the flat weld or at least one spot weld interconnects at least an entire circumference of the first tube and second tube in the region of at least one tube section.

17. The catheter shaft according to claim 15, wherein the reactive groups are selected from the group comprising carbonic acid, carbonic acid chloride, amide, carbonic acid anhydride, ester, lactone, lactam, nitrile and thioester.

18. The catheter shaft according to claim 15, wherein the polymeric material of the second tube is selected from the group comprising polyamide, PEBA (polyether block amide), polyester or TPU (thermoplastic polyurethane elastomers).

19. The catheter shaft according to claim 15, wherein the first tube is made of PVDF (polyvinylidene fluoride) grafted with maleic acid anhydride as one of the reactive groups, and the second tube is made of polyamide 12 or PEBA (polyether block amide).

20. The catheter shaft according to claim 15, wherein the tubes remain welded to one another, unchanged, at a pressure of 20 bar for ≥1 min.

21. The catheter shaft according to claim 15, wherein the catheter shaft is included in a medical device.

22. The medical device according to claim 21, selected from the group comprising a catheter stent insertion device or a balloon dilation catheter, in particular in an RX (rapid exchange) or over the wire design.

23. The catheter shaft according to claim 15, wherein the fluorinated copolymer is a copolymer of a polymer selected from the group comprising ETFE (polytetrafluorothylene+ethylene), C-ETFE (polychlorotrifluoroethylene+ethylene), PFA (polytetrafluoroethylene+perfluoropropylether), FEP (polytetrafluoroethylene+perfluoropropylene), PCTFE (polychlorotrifluoroethylene), PVF (polyvinyl fluoride) and PVDF (polyvinylidene fluoride).

* * * * *